US008989346B2

(12) United States Patent
Yoshikawa

(10) Patent No.: US 8,989,346 B2
(45) Date of Patent: Mar. 24, 2015

(54) BONE MINERAL DENSITY ANALYSIS METHOD, BONE MINERAL DENSITY ANALYSIS APPARATUS, AND RECORDING MEDIUM

(71) Applicant: FUJIFILM Corporation, Tokyo (JP)

(72) Inventor: Kenji Yoshikawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 266 days.

(21) Appl. No.: 13/722,994

(22) Filed: Dec. 20, 2012

(65) Prior Publication Data

US 2013/0170614 A1 Jul. 4, 2013

(30) Foreign Application Priority Data

Dec. 28, 2011 (JP) .................................. 2011-287749
Feb. 28, 2012 (JP) .................................. 2012-040892

(51) Int. Cl.
*A61B 6/00* (2006.01)
*G01N 23/087* (2006.01)

(52) U.S. Cl.
CPC ................. *A61B 6/505* (2013.01); *A61B 6/405* (2013.01); *A61B 6/482* (2013.01); *A61B 6/5217* (2013.01); *A61B 6/583* (2013.01)
USPC ................... 378/54; 378/55; 378/56; 378/45; 378/62; 378/98.9

(58) Field of Classification Search
CPC .......... A61B 6/583; A61B 6/032; G21K 1/10; H01J 2235/081; G01N 2333/916
USPC ............................ 378/54, 55, 56, 45, 62, 98.9
See application file for complete search history.

(56) References Cited

U.S. PATENT DOCUMENTS

| 4,864,594 | A | * | 9/1989 | Inbar et al. ......................... 378/5 |
| 5,379,997 | A | | 1/1995 | Ohta |
| 7,544,327 | B2 | * | 6/2009 | Chung et al. ................ 422/82.05 |
| 7,746,976 | B2 | * | 6/2010 | Huo et al. ........................ 378/54 |
| 7,965,813 | B2 | * | 6/2011 | Huo et al. ........................ 378/54 |

FOREIGN PATENT DOCUMENTS

| JP | 7-072253 A | 3/1995 |
| JP | 8-266529 A | 10/1996 |
| JP | 9-024039 A | 1/1997 |
| JP | 2006-334046 A | 12/2006 |
| JP | 2010-200824 A | 9/2010 |
| JP | 2010-206067 A | 9/2010 |
| WO | WO2008/044439 A1 | 4/2008 |

* cited by examiner

*Primary Examiner* — Nikita Wells
(74) *Attorney, Agent, or Firm* — McGinn IP Law Group, PLLC

(57) ABSTRACT

From radiation images obtained by driving radiation tube with a plurality of tube voltages, including a normal tube voltage, a density gradient with respect to at least two sections of a reference substance having different radiation transmission characteristics is obtained for each of the plurality of tube voltages prior to obtaining a bone mineral density. If a radiation image captured for obtaining a bone mineral density is determined to have been captured under a tube voltage other than the normal tube voltage, an image signal representing the image and/or a bone mineral density analysis result is corrected so as to correspond to that which should have been obtained if the image had been captured under the normal tube voltage based on the relationship between the density gradient in the image and the density gradient in the radiation image captured under the normal tube voltage.

16 Claims, 5 Drawing Sheets

BONE MINERAL DENSITY ANALYSIS METHOD, BONE MINERAL DENSITY ANALYSIS APPARATUS, AND RECORDING MEDIUM

BACKGROUND OF THE INVENTION

1. Field of the Invention

The present invention generally relates to a bone mineral density analysis method and more particularly to a bone mineral density analysis method using a radiation image of an analysis target bone portion.

The invention also relates to a system for implementing the bone mineral density analysis method described above and a computer readable recording medium on which is recorded a program for causing a computer to perform the method.

2. Description of the Related Art

Heretofore, in order to give a diagnosis for osteoporosis and the like, analysis methods that use a radiation image of an analysis target bone portion to obtain a bone mineral density of the bone portion have been known. As one of such bone mineral density analysis methods which can be performed relatively easily, a so-called MD (Microdensitometry) method is known. Basically, in the MD method, radiation generated from a radiation tube is projected simultaneously onto an analysis target bone portion and a reference substance having a plurality of sections with different radiation transmission characteristics to obtain a radiation image representing the bone portion and the reference substance by detecting radiation transmitted through the bone portion and reference substance with an X-ray film or the like, and a bone mineral density of the bone portion is obtained based on a radiation transmission characteristic of a section of the reference substance having the same density as that of the bone portion in the radiation image.

As for the reference substance, an aluminum slope whose thickness varies continuously is generally used and it is often the case that a thickness of the aluminum slope corresponding to the radiation transmission characteristic is defined as the index representing the bone mineral density.

Among the MD methods, a DIP (Digital Image Processing) method in which a radiation detecting body capable of providing a digital image signal representing a radiation image is used and a bone mineral density is obtained by processing the digital image signal is widely known as described, for example, in Japanese Unexamined Patent Publication No. 2006-334046, Domestic Re-publication of PCT International Publication for Patent Applications No. 2008-044439, and Japanese Unexamined Patent Publication No. 2010-200824. The bone mineral density analysis by the DIP method is getting more and more popular as it is easy to operate and requires only a short time.

In the bone mineral density analysis by DIP method described above, if the tube voltage of the radiation tube is different when capturing a radiation image by projecting radiation onto an analysis target bone portion and reference substance, such as the aluminum slope or the like, the analysis may indicate an erroneous result. Consequently, in the bone mineral density analysis by DIP method, the tube voltage of the radiation tube is set to a specific normal tube voltage (e.g., 50 kV) when capturing a radiation image in order to obtain a universal analysis result.

In order to make bone mineral density analysis results to be highly reliable, it is necessary that the tube voltage must be set accurately to the normal tube voltage when capturing a radiation image. Even when the tube voltage is set to the normal tube voltage, however, the actual tube voltage, i.e., the effective tube voltage may sometimes differ from the normal tube voltage due to a temporal change in the characteristics of the radiation tube.

In order to prevent such cases, measures have been taken, such as, measuring the tube voltage of the radiation tube by a tube voltmeter and calibrating such that the setting value of the tube voltage corresponds to the effective value. The tube voltmeter is very expensive, however, and it is undesirable to permanently provide a voltmeter in each medical institution, such as a hospital or the like, from the viewpoint of cost for bone mineral density analysis.

The present invention has been developed in view of the circumstances described above and it is an object of the present invention to provide a bone mineral density analysis method capable of obtaining universal bone mineral density analysis results even if the effective voltage of the radiation tube is different from the normal tube voltage.

It is a further object of the present invention to provide a bone mineral density analysis system for implementing the bone mineral density analysis method and a computer readable recording medium on which is recorded a program for causing a computer to perform the method.

SUMMARY OF THE INVENTION

A first bone mineral density analysis method of the present invention is a method based on the DIP method described above, that is, the method including the steps of:

projecting radiation generated from a radiation tube simultaneously onto an analysis target bone portion and a reference substance having a plurality of sections with different radiation transmission characteristics;

obtaining a radiation image representing the bone portion and the reference substance by detecting radiation transmitted through the bone portion and the reference substance with a radiation detecting body;

obtaining a bone mineral density of the bone portion based on a radiation transmission characteristic of a section of the reference substance that indicates the same density as that of the analysis target bone portion in the radiation image;

sequentially changing an image capturing condition to a plurality of different states, including a normal state, and obtaining a radiation image of the reference substance under each state prior to obtaining the bone mineral density;

obtaining a density gradient with respect to at least two sections of the reference substance having different radiation transmission characteristics for each of the plurality of different states of the image capturing condition from the radiation images of the reference substance; and correcting, if the radiation image captured for obtaining the bone mineral density is determined to have been captured under a state other than the normal state from a density gradient in the image, an image signal representing the image and/or a bone mineral density analysis result so as to correspond to that which should have been obtained if the image had been captured under the normal state based on the relationship between the density gradient in the image and the density gradient in the radiation image captured under the normal state.

A second bone mineral density analysis method of the present invention is a method based on the DIP method described above, that is, the method including the steps of:

projecting radiation generated from a radiation tube simultaneously onto an analysis target bone portion and a reference substance having a plurality of sections with different radiation transmission characteristics;

obtaining a radiation image representing the bone portion and the reference substance by detecting radiation transmitted through the bone portion and the reference substance with a radiation detecting body;

obtaining a bone mineral density of the bone portion based on a radiation transmission characteristic of a section of the reference substance that indicates the same density as that of the analysis target bone portion in the radiation image;

driving the radiation tube with a plurality of tube voltages, including a normal tube voltage, and obtaining a radiation image of the reference substance under each tube voltage prior to obtaining the bone mineral density;

obtaining a density gradient with respect to at least two sections of the reference substance having different radiation transmission characteristics for each of the plurality of tube voltages from the radiation images of the reference substance; and correcting, if the radiation image captured for obtaining the bone mineral density is determined to have been captured under a tube voltage other than the normal tube voltage from a density gradient in the image, an image signal representing the image and/or a bone mineral density analysis result so as to correspond to that which should have been obtained if the image had been captured under the normal tube voltage based on the relationship between the density gradient in the image and the density gradient in the radiation image captured under the normal tube voltage.

As for the reference substance described above, an aluminum member whose thickness varies continuously or in a stepwise manner may preferably be used.

Preferably, if that is the case, a bone mineral density is represented by a thickness of the aluminum member, as the index, as in the prior art.

In the bone mineral density analysis method of the present invention, it is preferable that a plurality of types of radiation detecting bodies having different radiation absorption characteristics is usable as the radiation detecting body, and that, if one of the plurality of radiation detecting bodies other than a specific radiation detecting body is used, an image signal representing the radiation image used for obtaining the bone mineral density and/or a bone mineral density analysis result is corrected so as to correspond to that which should be obtained if the specific radiation detecting body were used.

Preferably, a storage phosphor sheet is used as the specific radiation detecting body as it has been used widely in the bone mineral density analysis based on the DIP method and many data for evaluating bone mineral density analysis results are collected.

A first bone mineral density analysis system of the present invention is a system, including:

a radiation image capturing unit for projecting radiation generated from a radiation tube simultaneously onto an analysis target bone portion and a reference substance having a plurality of sections with different radiation transmission characteristics and obtaining a radiation image representing the bone portion and the reference substance by detecting radiation transmitted through the bone portion and the reference substance with a radiation detecting body;

a signal processing unit for obtaining a bone mineral density of the bone portion based on a radiation transmission characteristic of a section of the reference substance that indicates the same density as that of the analysis target bone portion in the radiation image;

a storage unit storing a density gradient with respect to at least two sections of the reference substance having different radiation transmission characteristics obtained, when an image capturing condition is sequentially changed to a plurality of different states, including a normal state, and a radiation image of the reference substance is obtained under each state prior to obtaining the bone mineral density, for each of the plurality of different states of the image capturing condition from the radiation images of the reference substance; and a correction unit for correcting, if the radiation image captured for obtaining the bone mineral density is determined to have been captured under a state other than the normal state from a density gradient in the image, an image signal representing the image and/or a bone mineral density analysis result so as to correspond to that which should have been obtained if the image had been captured under the normal state based on the relationship between the density gradient in the image and the density gradient in the radiation image captured under the normal state.

A second bone mineral density analysis system of the present invention is a system, including:

a radiation image capturing unit for projecting radiation generated from a radiation tube simultaneously onto an analysis target bone portion and a reference substance having a plurality of sections with different radiation transmission characteristics and obtaining a radiation image representing the bone portion and the reference substance by detecting radiation transmitted through the bone portion and the reference substance with a radiation detecting body;

a signal processing unit for obtaining a bone mineral density of the bone portion based on a radiation transmission characteristic of a section of the reference substance that indicates the same density as that of the analysis target bone portion in the radiation image;

a storage unit storing a density gradient with respect to at least two sections of the reference substance having different radiation transmission characteristics obtained, when the radiation tube is driven with a plurality of tube voltages, including a normal tube voltage, and a radiation image of the reference substance is obtained under each tube voltage prior to obtaining the bone mineral density, for each of the plurality of tube voltages from the radiation images of the reference substance; and a correction unit for correcting, if the radiation image captured for obtaining the bone mineral density is determined to have been captured under a tube voltage other than the normal tube voltage from a density gradient in the image, an image signal representing the image and/or a bone mineral density analysis result so as to correspond to that which should have been obtained if the image had been captured under the normal tube voltage based on the relationship between the density gradient in the image and the density gradient in the radiation image captured under the normal tube voltage.

A first recording medium of the present invention is a computer readable recording medium on which is recorded a program for causing a computer to perform a bone mineral density analysis method, the medium recording the steps of:

projecting radiation generated from a radiation tube simultaneously onto an analysis target bone portion and a reference substance having a plurality of sections with different radiation transmission characteristics;

obtaining a radiation image representing the bone portion and the reference substance by detecting radiation transmitted through the bone portion and the reference substance with a radiation detecting body;

obtaining a bone mineral density of the bone portion based on a radiation transmission characteristic of a section of the reference substance that indicates the same density as that of the analysis target bone portion in the radiation image;

sequentially changing an image capturing condition to a plurality of different states, including a normal state, and obtaining a radiation image of the reference substance under each state prior to obtaining the bone mineral density;

obtaining a density gradient with respect to at least two sections of the reference substance having different radiation transmission characteristics for each of the plurality of different states of the image capturing condition from the radiation images of the reference substance; and correcting, if the radiation image captured for obtaining the bone mineral density is determined to have been captured under a state other than the normal state from a density gradient in the image, an image signal representing the image and/or a bone mineral density analysis result so as to correspond to that which should have been obtained if the image had been captured under the normal state based on the relationship between the density gradient in the image and the density gradient in the radiation image captured under the normal state.

A second recording medium of the present invention is a computer readable recording medium on which is recorded a program for causing a computer to perform a bone mineral density analysis method, the medium recording the steps of:

projecting radiation generated from a radiation tube simultaneously onto an analysis target bone portion and a reference substance having a plurality of sections with different radiation transmission characteristics;

obtaining a radiation image representing the bone portion and the reference substance by detecting radiation transmitted through the bone portion and the reference substance with a radiation detecting body;

obtaining a bone mineral density of the bone portion based on a radiation transmission characteristic of a section of the reference substance that indicates the same density as that of the analysis target bone portion in the radiation image;

driving the radiation tube with a plurality of tube voltages, including a normal tube voltage, and obtaining a radiation image of the reference substance under each tube voltage prior to obtaining the bone mineral density;

obtaining a density gradient with respect to at least two sections of the reference substance having different radiation transmission characteristics for each of the plurality of tube voltages from the radiation images of the reference substance; and correcting, if the radiation image captured for obtaining the bone mineral density is determined to have been captured under a tube voltage other than the normal tube voltage from a density gradient in the image, an image signal representing the image and/or a bone mineral density analysis result so as to correspond to that which should have been obtained if the image had been captured under the normal tube voltage based on the relationship between the density gradient in the image and the density gradient in the radiation image captured under the normal tube voltage.

As described above, the first bone mineral density analysis method of the present invention includes the steps of: projecting radiation generated from a radiation tube simultaneously onto an analysis target bone portion and a reference substance having a plurality of sections with different radiation transmission characteristics; obtaining a radiation image representing the bone portion and the reference substance by detecting radiation transmitted through the bone portion and the reference substance with a radiation detecting body; obtaining a bone mineral density of the bone portion based on a radiation transmission characteristic of a section of the reference substance that indicates the same density as that of the analysis target bone portion in the radiation image; sequentially changing an image capturing condition to a plurality of different states, including a normal state, and obtaining a radiation image of the reference substance under each state prior to obtaining the bone mineral density; obtaining a density gradient with respect to at least two sections of the reference substance having different radiation transmission characteristics for each of the plurality of different states of the image capturing condition from the radiation images of the reference substance; and correcting, if the radiation image captured for obtaining the bone mineral density is determined to have been captured under a state other than the normal state from a density gradient in the image, an image signal representing the image and/or a bone mineral density analysis result so as to correspond to that which should have been obtained if the image had been captured under the normal state based on the relationship between the density gradient in the image and the density gradient in the radiation image captured under the normal state. Therefore, even if the image capturing condition is deviated from the normal state, the first bone mineral density analysis method of the present invention may obtain a universal bone mineral analysis result, i.e., the same analysis result as that which should be obtained if the image were captured under the normal state of the image capturing condition.

As described above, the second bone mineral density analysis method of the present invention includes the steps of: driving the radiation tube with a plurality of tube voltages, including a normal tube voltage, and obtaining a radiation image of the reference substance under each tube voltage prior to obtaining the bone mineral density; obtaining a density gradient with respect to at least two sections of the reference substance having different radiation transmission characteristics for each of the plurality of tube voltages from the radiation images of the reference substance; and correcting, if the radiation image captured for obtaining the bone mineral density is determined to have been captured under a tube voltage other than the normal tube voltage from a density gradient in the image, an image signal representing the image and/or a bone mineral density analysis result so as to correspond to that which should have been obtained if the image had been captured under the normal tube voltage based on the relationship between the density gradient in the image and the density gradient in the radiation image captured under the normal tube voltage. Therefore, even if the effective tube voltage of the radiation tube is deviated from the normal tube voltage, the second bone mineral density analysis method of the present invention may obtain a universal bone mineral analysis result, i.e., the same analysis result as that which should be obtained if the image were captured under the normal tube voltage.

The first bone mineral density analysis system of the present invention is a system, including: a radiation image capturing unit for projecting radiation generated from a radiation tube simultaneously onto an analysis target bone portion and a reference substance having a plurality of sections with different radiation transmission characteristics and obtaining a radiation image representing the bone portion and the reference substance by detecting radiation transmitted through the bone portion and the reference substance with a radiation detecting body; a signal processing unit for obtaining a bone mineral density of the bone portion based on a radiation transmission characteristic of a section of the reference substance that indicates the same density as that of the analysis target bone portion in the radiation image; a storage unit storing a density gradient with respect to at least two sections of the reference substance having different radiation transmission characteristics obtained, when an image capturing condition is sequentially changed to a plurality of different states, including a normal state, and a radiation image of the reference substance is obtained under each state prior to obtaining the bone mineral density, for each of the plurality of different states of the image capturing condition from the radiation images of the reference substance; and a correction unit for correcting, if the radiation image captured for obtaining the bone mineral density is determined to have been captured under a state other than the normal state from a density gradient in the image, an image signal representing the image and/or a bone mineral density analysis result so as to correspond to that which should have been obtained if the image had been captured under the normal state based on the relationship between the density gradient in the image and the density gradient in the radiation image captured under the normal state. Therefore, the first bone mineral density analysis system of the present invention may implement the first bone mineral density analysis method of the present invention described above.

The second bone mineral density analysis system of the present invention is a system, including: a radiation image capturing unit for projecting radiation generated from a radiation tube simultaneously onto an analysis target bone portion and a reference substance having a plurality of sections with different radiation transmission characteristics and obtaining a radiation image representing the bone portion and the reference substance by detecting radiation transmitted through the bone portion and the reference substance with a radiation detecting body; a signal processing unit for obtaining a bone mineral density of the bone portion based on a radiation transmission characteristic of a section of the reference substance that indicates the same density as that of the analysis target bone portion in the radiation image; a storage unit storing a density gradient with respect to at least two sections of the reference substance having different radiation transmission characteristics obtained, when the radiation tube is driven with a plurality of tube voltages, including a normal tube voltage, and a radiation image of the reference substance is obtained under each tube voltage prior to obtaining the bone mineral density, for each of the plurality of tube voltages from the radiation images of the reference substance; and a correction unit for correcting, if the radiation image captured for obtaining the bone mineral density is determined to have been captured under a tube voltage other than the normal tube voltage from a density gradient in the image, an image signal representing the image and/or a bone mineral density analysis result so as to correspond to that which should have been obtained if the image had been captured under the normal tube voltage based on the relationship between the density gradient in the image and the density gradient in the radiation image captured under the normal tube voltage. Therefore, the second bone mineral density analysis system of the present invention may implement the second bone mineral density analysis method of the present invention described above.

The first recording medium of the present invention is a computer readable recording medium on which is recorded a program for causing a computer to perform a bone mineral density analysis method, the medium recording the steps of: projecting radiation generated from a radiation tube simultaneously onto an analysis target bone portion and a reference substance having a plurality of sections with different radiation transmission characteristics; obtaining a radiation image representing the bone portion and the reference substance by detecting radiation transmitted through the bone portion and the reference substance with a radiation detecting body; obtaining a bone mineral density of the bone portion based on a radiation transmission characteristic of a section of the reference substance that indicates the same density as that of the analysis target bone portion in the radiation image; sequentially changing an image capturing condition to a plurality of different states, including a normal state, and obtaining a radiation image of the reference substance under each state prior to obtaining the bone mineral density; obtaining a density gradient with respect to at least two sections of the reference substance having different radiation transmission characteristics for each of the plurality of different states of the image capturing condition from the radiation images of the reference substance; and correcting, if the radiation image captured for obtaining the bone mineral density is determined to have been captured under a state other than the normal state from a density gradient in the image, an image signal representing the image and/or a bone mineral density analysis result so as to correspond to that which should have been obtained if the image had been captured under the normal state based on the relationship between the density gradient in the image and the density gradient in the radiation image captured under the normal state. Therefore, the medium may be used for implementing the first bone mineral density analysis method of the present invention described above.

The second recording medium of the present invention is a computer readable recording medium on which is recorded a program for causing a computer to perform a bone mineral density analysis method, the medium recording the step of: projecting radiation generated from a radiation tube simultaneously onto an analysis target bone portion and a reference substance having a plurality of sections with different radiation transmission characteristics; obtaining a radiation image representing the bone portion and the reference substance by detecting radiation transmitted through the bone portion and the reference substance with a radiation detecting body; obtaining a bone mineral density of the bone portion based on a radiation transmission characteristic of a section of the reference substance that indicates the same density as that of the analysis target bone portion in the radiation image; driving the radiation tube with a plurality of tube voltages, including a normal tube voltage, and obtaining a radiation image of the reference substance under each tube voltage prior to obtaining the bone mineral density; obtaining a density gradient with respect to at least two sections of the reference substance having different radiation transmission characteristics for each of the plurality of tube voltages from the radiation images of the reference substance; and correcting, if the radiation image captured for obtaining the bone mineral density is determined to have been captured under a tube voltage other than the normal tube voltage from a density gradient in the image, an image signal representing the image and/or a bone mineral density analysis result so as to correspond to that which should have been obtained if the image had been captured under the normal tube voltage based on the relationship between the density gradient in the image and the density gradient in the radiation image captured under the normal tube voltage. Therefore, the medium may be used for implementing the second bone mineral density analysis method of the present invention described above.

DESCRIPTION OF THE PREFERRED EMBODIMENTS

Figure 1:
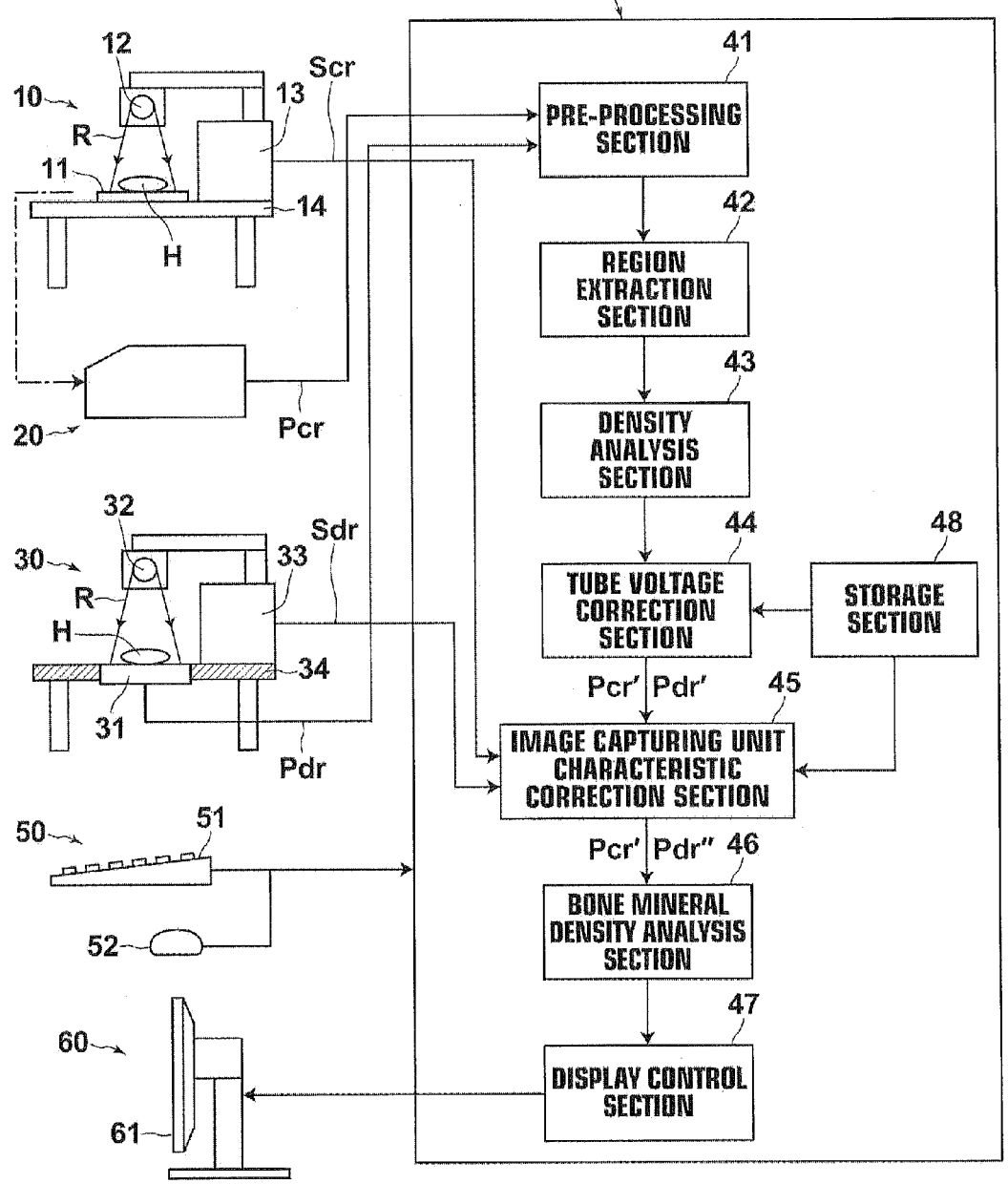
FIG. 1 is a view of a system for implementing a bone mineral density analysis method according to an embodiment of the present invention, schematically illustrating the configuration thereof.

Hereinafter, embodiments of the present invention will be described in detail with reference to the accompanying drawings. FIG. 1 is a view of a system for implementing a bone mineral density analysis method according to an embodiment of the present invention, schematically illustrating the configuration thereof. The present system performs bone mineral density analysis by the DIP method described above. As illustrated in FIG. 1, the system includes: a first image capturing unit 10 for capturing and recording on a recording medium a radiation image of a subject, including a target bone portion for bone mineral density analysis; a reading unit 20 for reading the radiation image captured by the first image capturing unit 10 from the recording medium and outputting a digital image signal Pcr representing the radiation image; a second image capturing unit 30 for capturing a radiation image of the subject, including the target bone portion for bone mineral density analysis, and directly outputting a digital image signal Pdr representing the radiation image; a signal processing unit 40 for obtaining a bone mineral content of the analysis target bone portion based on the digital signal Pcr or Pdr; an input unit 50 for giving various instructions to the signal processing unit 40; and a display unit 60 for displaying a result of the bone mineral density analysis.

The first image capturing unit 10 is, by way of example, a unit that stores and records radiation image information of a subject on a storage phosphor sheet, as the radiation detecting body, as described, for example, in Japanese Unexamined Patent Publication Nos. 8(1996)-266529 and 9(1997)-024039, and, in particular, a cassette 11 accommodating a storage phosphor sheet is used here. That is, the first image capturing unit 10 includes an image capturing platform 14 on which the cassette 11 is placed in substantially flatly, a radiation tube 12 for emitting radiation R (X-ray, by way of example) toward the cassette from above, and an image capturing control section 13 for drive-controlling the radiation tube 12.

In the first image capturing unit 10, the radiation tube 12 is driven with a subject H being placed on the cassette 11 and when radiation R is projected from the radiation tube 12 toward the cassette 11, energy of radiation R transmitted through the subject H is stored in the storage phosphor sheet. That is, transmitted radiation representing image information of the subject H is recorded in the storage phosphor sheet.

The reading unit 20 is a unit for reading the radiation image information of the subject H from the storage phosphor sheet. Although such type of reading device is described in detail, for example, in U.S. Pat. No. 5,379,997, basics of the unit are described briefly below. In the reading unit 20, the storage phosphor sheet taken out from the cassette 11 is two-dimensionally scanned with reading light, such as laser light, and photostimulated luminescence emitted from a portion of the storage phosphor sheet by receiving the reading light is read by a photoelectric conversion means, whereby an image signal representing the radiation image information recorded in the sheet is obtained. The image signal is subjected to A/D conversion to obtain the digital image signal Pcr described above for subsequent signal processing.

The second image capturing unit 30 includes a radiation tube 32, an image capturing control section 33, and an image capturing platform 34 which are identical to the radiation tube 12, image capturing control section 13, and image capturing platform 14 of the first image capturing unit 10 respectively. But, the second image capturing unit 30 basically differs from the first image capturing unit 10 in that it includes a radiation detector 31, instead of the cassette 11, onto which radiation R is projected. The aforementioned radiation detector 31 is a detector that outputs a radiation detection signal according to the energy level of the radiation received with respect to each pixel arranged in a matrix. The detection signal is subjected to an A/D conversion and outputted as an image signal Pdr representing a transmitted radiation image of the subject.

As for the radiation detector 31 described above, a detector formed of a scintillator that emits visible light by receiving radiation and a solid-state photo-detection element that detects the visible light layered on top of each other as described, for example, in Japanese Unexamined Patent Publication No. 7(1995)-072253 or a detector having a radiation photoconductive layer that receives radiation and outputs an electrical signal according to the energy of radiation received as described, for example, in Japanese Unexamined Patent Publication No. 2010-206067 may be used.

The signal processing unit 40 includes a pre-processing section 41 where the digital image signals Pcr and Pdr are inputted, and the following sections connected in series after the pre-processing unit: a region extraction section 42, a density analysis section 43, a tube voltage correction section 44, an image capturing unit characteristic correction section 45, a bone mineral density analysis section 46 and display control section 47. The signal processing unit 40 further includes a storage section 48 connected to the tube voltage correction section 44 and image capturing unit characteristic correction section 45.

The input unit 50 includes input means, such as a keyboard 51 and a mouse 52 and gives processing instructions to the signal processing unit 40 via these input means.

The display unit 60 includes a display means 61, such as a liquid crystal display or a CRT display, and displays a result of the bone mineral density analysis and the captured radiation image of the subject as required based on information inputted in a manner to be described later.

The signal processing unit 40, input unit 50, and display unit 60 described above may be formed of a computer system, such as a general personal computer.

Figure 2:
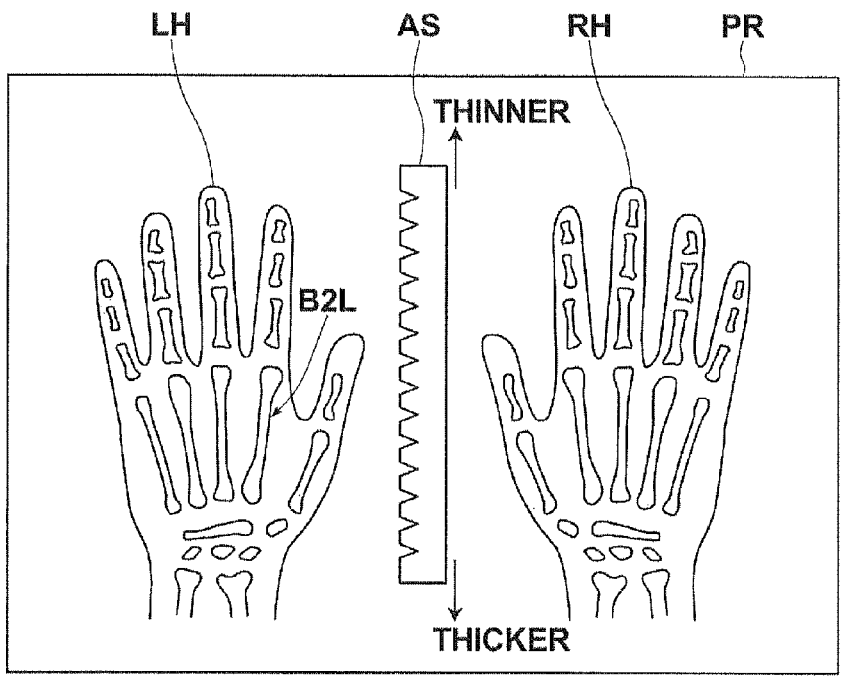
FIG. 2 illustrates an example radiation image captured for bone mineral density analysis.

Next, capturing of a radiation image for bone mineral density analysis will be described with reference to FIG. 2. Here, image capturing performed by the first image capturing unit 10 will be described first. When performing the image capturing, the cassette 11 accommodating a storage phosphor sheet is placed on the image capturing platform 14 of the first image capturing unit 10 and then left and right hands of a subject are placed on the cassette 11 with an aluminum plate, as the reference substance, being placed between the hands. The aluminum plate is a plate-like member whose thickness changes continuously. Instead of such type of aluminum slope, an aluminum plate-like member whose thickness changes in a stepwise manner may be used.

Under this state, the radiation tube 12 is driven by operating the image capturing control section 13 and radiation R emitted from the tube is projected onto the storage phosphor sheet of the cassette 11 by transmitting through the left and right hands as well as the aluminum slope. In the DIP method, image capturing is normally performed with the tube voltage of the radiation tube 12 being set to 50 kV. Also, in the present invention, the tube voltage is set to 50 kV. Note that the effective tube voltage tends to drop with time and may not sometimes get to 50 kV even if it is set so. The present embodiment prevents analysis error due to such tube voltage difference as will be described in detail later.

After the image capturing is completed, the cassette 11 is taken out from the first image capturing unit 10 and set in the reading unit 20. In the reading unit 20, radiation image information stored and recorded in the storage phosphor sheet in the cassette 11 in the manner described above is read and a digital image signal Pcr representing the radiation image information is obtained. The radiation image represented by the digital image signal Pcr may be reproduced and displayed by inputting the signal Pcr to the display unit 60 or the like and, if displayed, the radiation image appears like that shown in FIG. 2. That is, the radiation image PR includes a left hand LH and a right hand RH of the subject, and an aluminum slope AS. The aluminum slope AS is set on the cassette 11 such that the thickness thereof gradually becomes thinner toward the finger tip direction of the left hand LH and right hand RH (toward the upper side in FIG. 2).

The digital image signal Pcr is inputted to the pre-processing section 41 of the signal processing unit 40 with identification information of the cassette 11 that has obtained the signal Pcr. Further, when the image capturing is performed in the first image capturing unit 10, image capturing information Scr which includes identification information of the first image capturing unit 10, identification information of the cassette 11, information indicating the image capturing order, and the like is inputted to the image capturing unit characteristic correction section 45 of the signal processing unit 40 from the image capturing control section 13.

Processing performed in the signal processing unit 40 will now be described. The digital image signal Pcr inputted to the signal processing unit 40 is subjected, in the pre-processing section 41, to correction of variations in the signal value arising from unevenness of the projected radiation or unevenness of reading characteristics of the reading unit 20, as well as to other types of processing requested as appropriate, and then inputted to the region extraction section 42.

Figure 3:
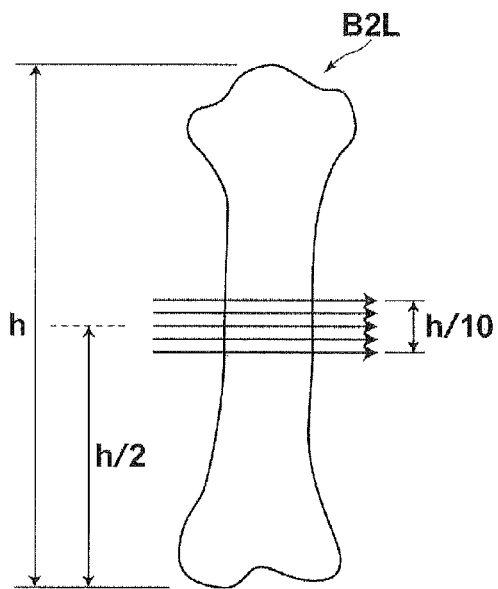
FIG. 3 illustrates an area from which an image signal is extracted for bone mineral density analysis.

The region extraction section 42 extracts a target region for bone mineral density analysis from the image represented by the digital image signal Pcr automatically by image processing or based on an instruction from the input unit. As bone mineral density analysis is normally performed on a second metacarpal bone B2L of the left hand in the DIP method, the second metacarpal bone B2L of the left hand is extracted also in the present embodiment. More specifically, a region of h/10 (FIG. 3) located in a central portion of the entire length of the second metacarpal bone B2L of the left hand is extracted.

Figure 4:
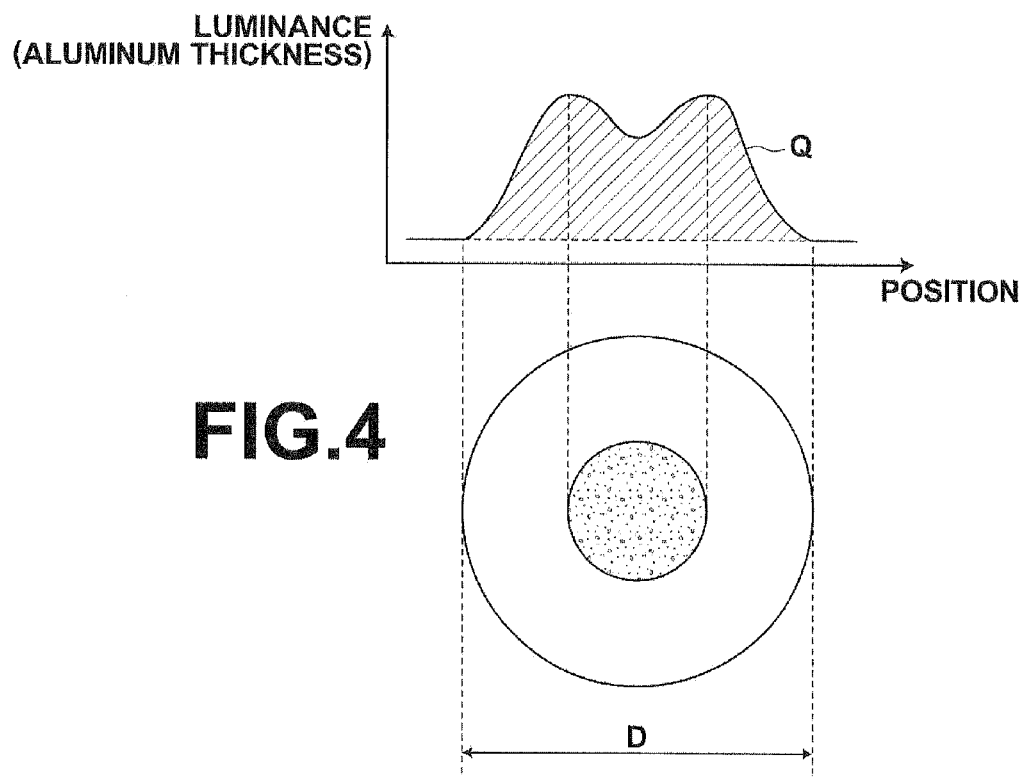
FIG. 4 illustrates an example density profile of a radiation image in the area described above.

Next, the density analysis section 43 obtains an average density of the extracted region described above. More specifically, the density analysis section 43 obtains a density profile in a direction traversing the second metacarpal bone B2L of the left hand in the region. If the density profile is represented by luminance instead of density, it appears like that shown by a curve Q in FIG. 4. Note that the reference symbol D represents a bone width. Such density profiles are obtained, for example, for a dozen points in the region along a length direction of the bone and an average profile is obtained through calculation.

In the past, the density of the average density profile is directly converted to the thickness of the aluminum slope (aluminum thickness), that is, the thickness of the aluminum slope portion corresponding to each point density of the profile in the radiation image is obtained and the value ΣGS/D [unit: mmAl (aluminum)] obtained by dividing the integrated value ΣGS of the aluminum thickness conversion values by the bone width D is determined to be the DIP value representing bone mineral content. With respect to the DIP value, a standard value for each gender and each age group is published, for example, by the Japanese Society for Bone and Mineral Research, and a bone mineral content is judged to be in a normal range if it falls within the range from 100 to 80% of each standard value.

Note that the DIP value=ΣGS/D described above may differ from the value obtain in the manner described above if an image capturing unit that uses a radiation detector, like the radiation detector 31 of the second image capturing unit 30, having a different radiation absorption characteristic from that of a storage phosphor sheet is employed instead of an image capturing unit that uses a storage phosphor sheet as the recording medium as in the first image capturing unit 10 or if the effective tube voltage is other than 50 kV. The standard values described above are defined for DIP values where a radiation image capturing is performed using a storage phosphor sheet with the tube voltage being set to 50 kV. If a diagnosis is given for bone mineral content using the standard values, therefore, it is necessary to correct the different DIP value described above so as to correspond to the DIP value where the storage phosphor sheet is used and the tube voltage is set to 50 kV.

Figure 5:
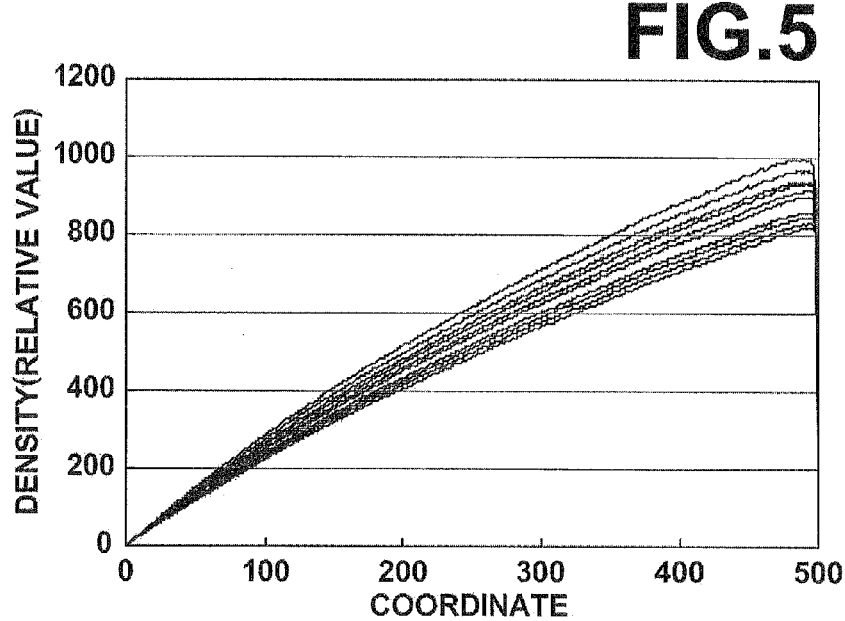
FIG. 5 is a graph illustrating the relationship between the thickness (coordinate) of an aluminum slope and image density produced by the radiation transmitted through the coordinate in a radiation image captured by a certain image capturing apparatus for each tube voltage value of the radiation tube.

Such correction will now be described. The present inventor has examined, when an aluminum slope image is captured by an image capturing unit that captures and records a radiation image in a storage phosphor sheet as in the first image capturing unit 10, how the relationship between the thickness of the aluminum slope and density in the captured radiation image may change according to the tube voltage of the radiation tube. FIG. 5 shows a result of the examination which is obtained prior to performing the radiation image capturing for bone mineral density analysis.

In FIG. 5, the horizontal axis represents the coordinate uniquely corresponding to the thickness of the aluminum slope while the vertical axis represents the density of the radiation image (relative value). The ten characteristic curves shown in the graph are those when the tube voltage is set to 47 kV, 48 kV, 49 kV, 50 kV, 51 kV, 52 kV, 53 kV, 54 kV, 55 kV, and 56 kV from the top. The tube voltages listed above are actually confirmed using a tube voltmeter, and not just being set in the image capturing control section.

As illustrated in the drawing, the gradient of each characteristic curve (density gradient) is clearly different for each tube voltage value. Taking advantage of this fact, in the present embodiment, the tube voltage correction section 44 shown in FIG. 1 obtains what kV of the effective tube voltage was at the time of the image capturing in the first image capturing unit 10 from the digital image signal Pcr representing the aluminum slope based on a gradient of the characteristic curve between a predetermined coordinates. For that purpose, a correspondence relationship between the gradient and tube voltage is stored in the storage section 48 and the tube voltage correction section 44 reads a tube voltage corresponding to the gradient obtained from the digital image signal Pcr. Then, the tube voltage correction section 44 corrects the digital image signal Pcr based on the read tube voltage and tube voltage of 50 kV. In order to know the gradient described above, it is only necessary to obtain the correspondence relationship between the coordinates and density with respect to at least two points of the aluminum slope.

Figure 6:
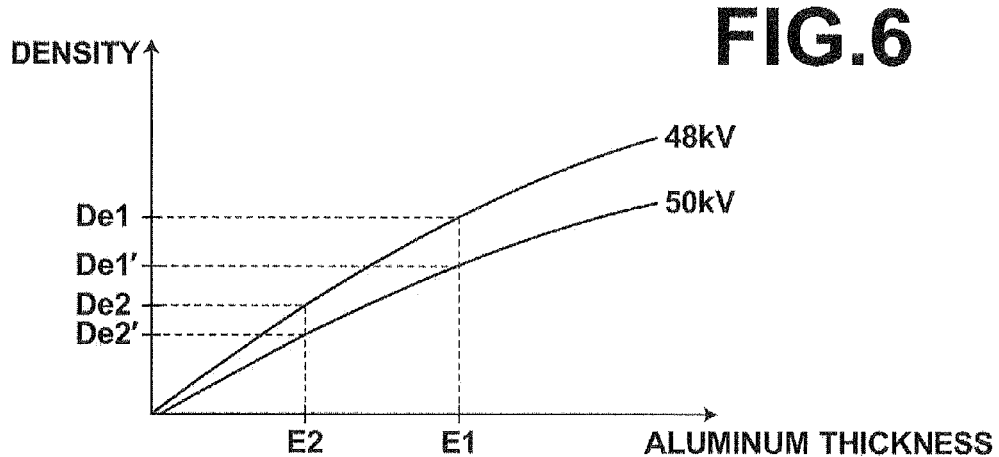
FIG. 6 illustrates how to correct difference in image density due to difference in tube voltage of the radiation tube.

For example, in the case where the effective tube voltage was 48 kV, the correction is made in the manner as shown in FIG. 6. That is, if the aluminum thickness (or radiation absorption characteristic) was E1, as illustrated in the drawing, the corresponding image density should be De1' if the effective voltage was 50 kV, but the image density is De1 since the effective voltage was 48 kV. In this case, the digital image signal Pcr representing the image density De1 is corrected to a value representing the image density De1'. Likewise, a digital image signal representing, for example, the image density De2 is corrected to a value representing the image density De2'. The correspondence relationship between pre-correction and post-correction digital image signals Pcr is stored in the storage section 48 in a form of lookup table for each effective voltage value. The tube voltage correction section 44 obtains a value of digital image signal Pcr after correction or a value to be used as a correction value. The correction is made for all digital image signals Pcr representing the average density profile described above and digital image signals Pcr representing the aluminum slope portion, and corrected digital image signals Pcr' are inputted to the image capturing unit characteristic correction section 45.

As described above, the image capturing unit characteristic correction section 45 has already received image capturing information Scr from the image capturing control unit 13 of the first image capturing unit 10, which includes identification information of the first image capturing unit 10, identification information of the cassette 11, information indicating image capturing order, and the like. If the original digital image signal Pcr of the inputted digital image signal Pcr' is determined to have been generated by the first image capturing unit 10 based on the image capturing information Scr or based on image capturing information appended to a digital image signal Pcr, the image capturing unit characteristic correction section 45 passes the inputted digital image signal Pcr' as it is and inputs to the bone mineral density analysis section 46.

The bone mineral density analysis section 46 obtains the DIP value=ΣGS/D described above. That is, the bone mineral density analysis section 46 converts the densities of the average density profile (Q in FIG. 4) represented by the digital image signal Pcr' to thicknesses of the aluminum slope (aluminum thicknesses) and obtains the DIP value by dividing the integrated value ΣGS of the aluminum thickness values by the bone width D. The bone mineral density analysis section 46 inputs information representing the DIP value=ΣGS/D obtained in the manner described above to the display control section 47. The display control section 47 causes the display means 61 of the display unit 60 to display the DIP value.

The DIP value displayed on the display means 61 in the manner described above is equal to that obtained when the effective tube voltage is 50 kV as it is based on the digital image signal Pcr' corrected by the tube voltage correction section 44. Consequently, the diagnosis of the bone mineral content made by the use of the standard value described above may become highly reliable. Note that the display means 61 of the display unit 60 may display not only the DIP value but also an outcome of the diagnosis, such as a ratio of the value to the standard value or a message like "no signs of osteoporosis" or the like.

Note that the correction may be made by first obtaining a DIP value=ΣGS/D based on the digital image signal Pcr and then correcting the DIP value so as to corresponds to the value obtained from the digital image signal Pcr' instead of correcting the digital image signal Pcr to the digital image signal Pcr'.

The standard value described above is set with respect to the DIP value when image capturing is performed using a storage phosphor sheet with a tube voltage being set to 50 kV, so that if the radiation image is captured by the first image capturing unit 10 that uses a storage phosphor sheet, there is no need to take into account the difference in DIP value due to difference in characteristics between image capturing units. Therefore, the digital image signal Pcr' is passed, as it is, through the image capturing unit characteristic correction section 45 as described above. Further, in the case where the effective tube voltage is confirmed to be 50 kV, the correction by the tube voltage correction section 44 described above is not performed as no correction is required for difference in DIP value due to difference in tube voltage.

Next, processing performed in the signal processing unit 40 in the case where image capturing is performed using the second image capturing unit 30 shown in FIG. 1 will be described. When image capturing is performed using the second image capturing unit 30, a digital image signal Pdr is inputted to the pre-processing section 41 and subjected to the same processing as that described above. When the image capturing is performed in the second image capturing unit 30, image capturing information Sdr similar to the image capturing information Scr described above is inputted to the image capturing unit characteristic correction section 45 of the signal processing unit 40 from the image capturing control section 33.

Then, in this case also, if it is detected by the tube voltage correction section 44 that the effective voltage was not 50 kV at the time of the image capturing, the correction processing identical to that when the radiation image was captured by the first image capturing unit is performed. The correction processing performed by the tube voltage correction section 44 is identical to that described above and is not elaborated upon further here. In FIG. 1, if a digital image signal Pdr is subjected to the correction processing, the corrected digital image signal is represented as Pdr'.

Figure 8:
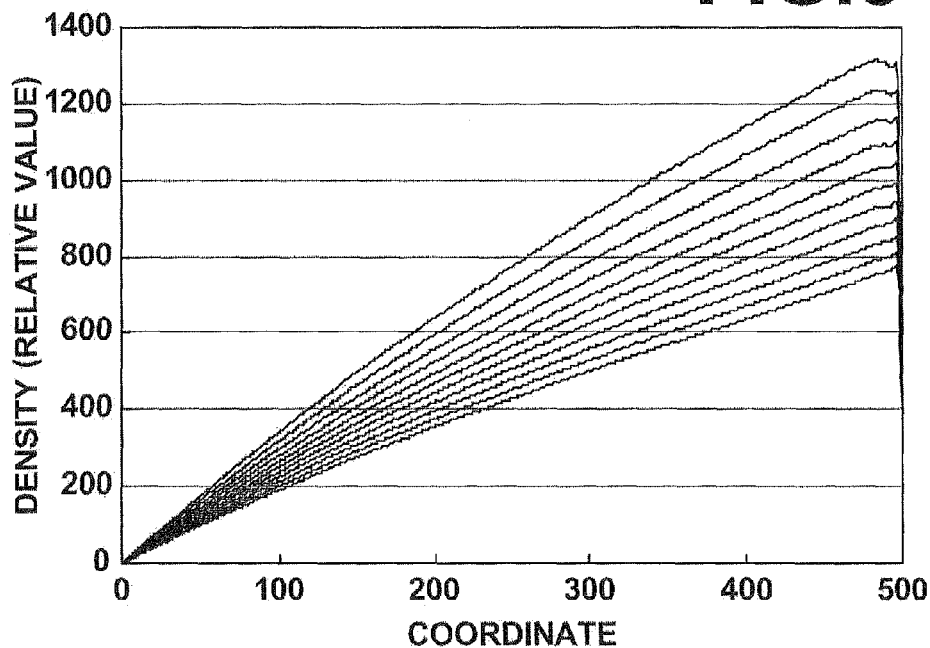
FIG. 8 is a graph illustrating the relationship between the thickness (coordinate) of an aluminum slope and image density produced by the radiation transmitted through the coordinate in a radiation image captured by another image capturing unit for each tube voltage value of the radiation tube.
Figure 9:
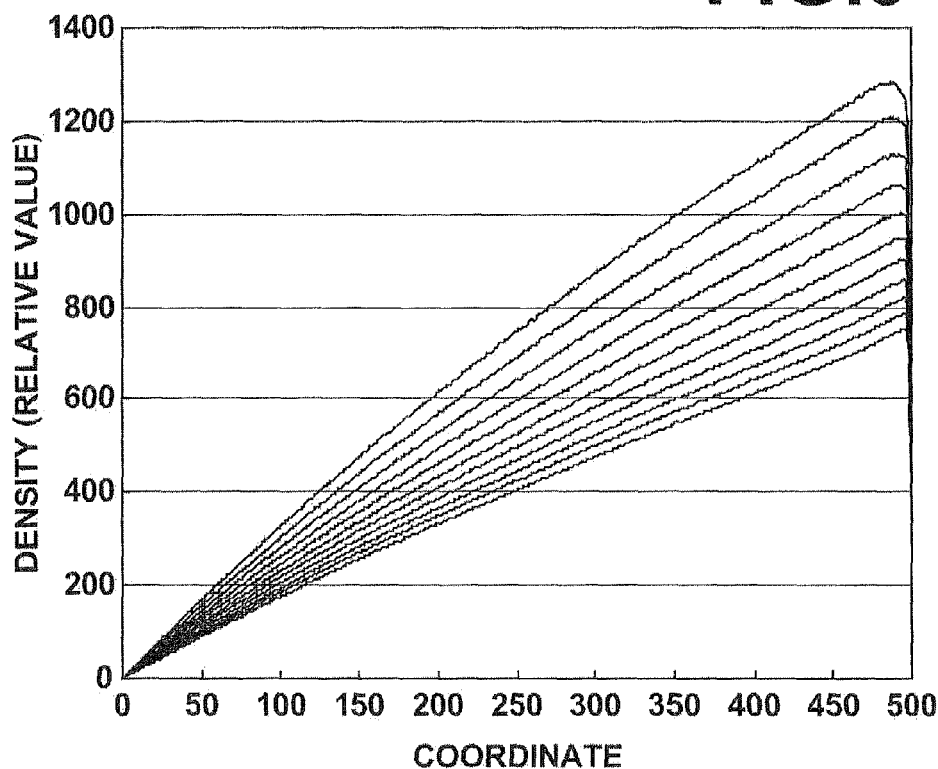
FIG. 9 is a graph illustrating the relationship between the thickness (coordinate) of an aluminum slope and image density produced by the radiation transmitted through the coordinate in a radiation image captured by still another image capturing unit for each tube voltage value of the radiation tube.

The relationship between the coordinate and density illustrated in FIG. 5, however, is unique to each image capturing unit and the relationship thereof when image capturing is performed by the second image capturing unit 30 is shown in FIG. 8. The radiation detector 31 of the second image capturing unit 30 is a detector formed of a scintillator and a solid-state photo-detection element made of GoS (gadolinium oxide sulfur) layered on top of each other. Although not shown in FIG. 1, a detector formed of a scintillator and a solid-state photo-detection element made of CsI (cesium iodide) layered on top of each other may also be used as the radiation detector and an image capturing unit that uses such a type of radiation detector will be hereinafter referred to as a third image capturing unit. FIG. 9 illustrates the relationship between the coordinate and density when image capturing is performed by the third image capturing unit.

Figure 7:
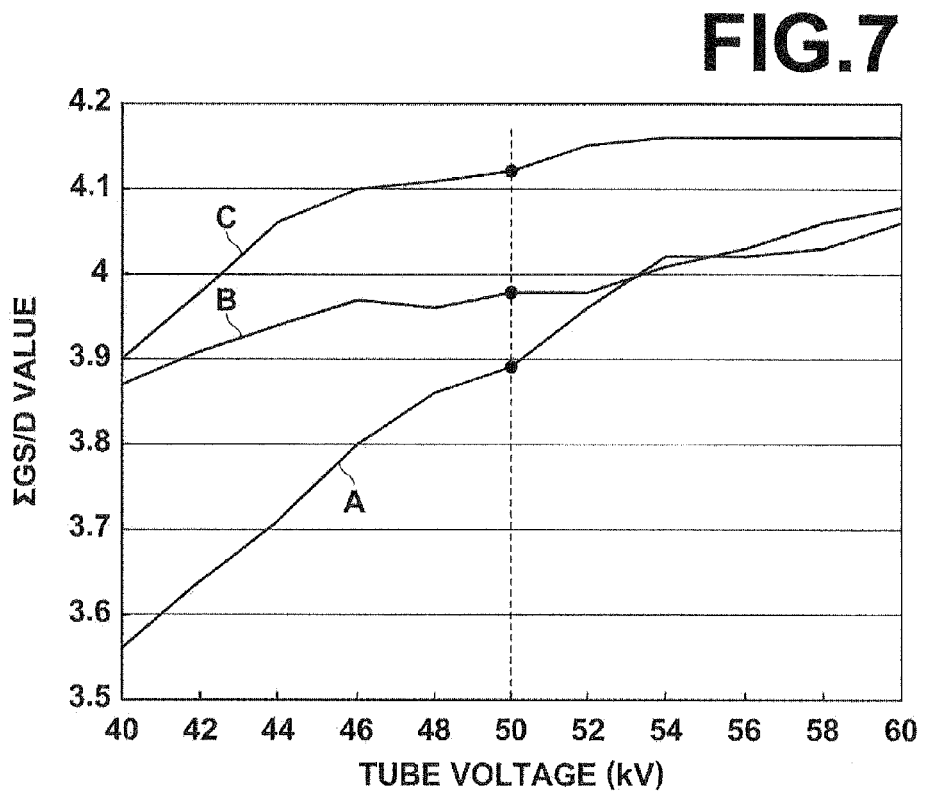
FIG. 7 is a graph illustrating the relationship between the tube voltage and ΣGS/D value for each type of image capturing unit.

In the mean time, the present inventor has captured radiation images of a certain common bone portion (which may be replaced with an aluminum plate member having a certain uniform thickness) by the first image capturing unit 10 and second image capturing unit 30 under various tube voltages and obtained a DIP value=ΣGS/D for each captured radiation image of the bone portion. FIG. 7 illustrates the result. In this case, the DIP value changes according to the value of the tube voltage at the time of image capturing, as described above. It is also known that the change characteristic differs with respect to each image capturing unit, as illustrated in FIG. 7. In FIG. 7, the reference symbol A represents the characteristic when image capturing was performed by the first image capturing unit 10, the reference symbol B represents the characteristic when image capturing was performed by the second image capturing unit 30, and the reference symbol C represents the characteristic when image capturing was performed by the third image capturing unit.

The present embodiment obtains the ΣGS/D value at the tube voltage of 50 kV and FIG. 7 shows that each ΣGS/D value at the tube voltage of 50 kV differs from image capturing unit to image capturing unit even though images of the common bone portion have been captured. The reason is that the storage phosphor sheet and two types of radiation detectors, including the radiation detector 31, are different in radiation absorption characteristic.

Here, in the case where radiation images of a bone portion different from the bone portion from which the characteristics shown in FIG. 7 have been obtained are captured, it can be said that the ratio between the three ΣGS/D values under the tube voltage of 50 kV is substantially identical to that of the characteristics of FIG. 7. Further, the ΣGS/D value corresponds to image density. In view of these described above, if it is determined that the original digital image signal Pdr of the inputted digital image signal Pdr' was captured by the second image capturing unit 30, the image capturing unit characteristic correction section 45 in FIG. 1 converts a signal with respect to the aluminum slope AS portion of the digital image signal Pdr' such that a density Dd' represented by the signal with respect to the aluminum slope portion becomes a density Dd"=kDd'. Here, k represents the ratio of the ΣGS/D value of the characteristic A to that of the characteristic B at the tube voltage of 50 kV in FIG. 7. The aforementioned determination may be made based on the image capturing information Sdr inputted to the image capturing unit characteristic correction section 45 from the image capturing control section 33, image capturing information appended to the digital image signal Pdr, or the like.

The converted digital image signal Pdr" is inputted to the bone mineral density analysis section 46. Based on the digital image signal Pdr", the bone mineral density analysis section 46 obtains a DIP value=ΣGS/D in the same manner as described above and the display control section 47 causes the display means 61 of the display unit 60 to display the DIP value. The aforementioned conversion may be performed through calculation in each case or pairs of signals before and after the conversion may be stored in a storage means in the form of a LUT and the conversion may be performed by referring to the LUT.

Instead of converting the signal with respect to the aluminum slope AS portion of the digital image signal Pdr', only a signal with respect to the second metacarpal bone of the left hand of the digital image signal Pdr' may be converted such that the same effect is obtained. Such conversion may be performed after extracting a density profile of the aluminum slope AS or second metacarpal bone of the left hand and on the digital image signal Pdr' representing the density profile, or on a digital image signal Pdr' of the corresponding area in the image before the extraction of the density profile.

The DIP value displayed on the display unit 60 in the manner described above shows the same value as that when a radiation image is captured by the first image capturing unit 10 if the image capturing target is the same bone portion. Consequently, the diagnosis of the bone mineral content made by the use of the normal value described above may become highly reliable.

In the present embodiment, the digital image signal Pdr' is converted to the digital image signal Pdr" and the DIP value=ΣGS/D is obtained from the converted digital image signal Pdr". But, an arrangement may be adopted in which the DIP value=ΣGS/D is obtained from the digital image signal. Pdr' and the obtained DIP value=ΣGS/D is converted so as to correspond to the DIP value=ΣGS/D in the case where the radiation image is captured by the first image capturing unit 10 based on the relationship shown in FIG. 7.

Further, in preparation for the case where the correction by the tube voltage correction section 44 and the correction by the image capturing unit characteristic correction section 45 are both performed, an arrangement may be adopted in which a LUT defining conversion values for performing both corrections at the same time is generated and stored in a storage means, and the both corrections are performed at a time using the LUT.

In the case where a radiation image is captured by the third image capturing unit described above, a conversion similar to that of the digital image signal Pdr' to the digital image signal Pdr' may be performed on a digital image signal outputted therefrom and inputted to the pre-processing section 41, as well as being subjected to the tube voltage correction as required. In this case, however, a ratio of the ΣGS/D value of the characteristic A to the ΣGS/D value of the characteristic C at the tube voltage of 50 kV in FIG. 7 is used as the value of k.

Further, a program having each step for performing the bone mineral density analysis method of the present invention described above may be recorded on a computer readable recording medium and a computer may be caused to perform each step using the recording medium.

What is claimed is:

1. A bone mineral density analysis method implemented by a bone mineral analysis system, the method comprising the steps of:

projecting radiation generated from a radiation tube simultaneously onto an analysis target bone portion and a reference substance having a plurality of sections with different radiation transmission characteristics;

obtaining a radiation image representing the bone portion and the reference substance by detecting radiation transmitted through the bone portion and the reference substance with a radiation detecting body;

obtaining a bone mineral density of the bone portion based on a radiation transmission characteristic of a section of the reference substance that indicates the same density as that of the analysis target bone portion in the radiation image;

sequentially changing an image capturing condition to a plurality of different states, including a normal state, and obtaining a radiation image of the reference substance under each state prior to obtaining the bone mineral density;

obtaining a density gradient with respect to at least two sections of the reference substance having different radiation transmission characteristics for each of the plurality of different states of the image capturing condition from the radiation images of the reference substance; and correcting, if the radiation image captured for obtaining the bone mineral density is determined to have been captured under a state other than the normal state from a density gradient in the image, an image signal representing the image and/or a bone mineral density analysis result so as to correspond to that which should have been obtained if the image had been captured under the normal state based on the relationship between the density gradient in the image and the density gradient in the radiation image captured under the normal state.

2. A bone mineral density analysis method implemented by a bone mineral analysis system, the method comprising the steps of:

projecting radiation generated from a radiation tube simultaneously onto an analysis target bone portion and a reference substance having a plurality of sections with different radiation transmission characteristics;

obtaining a radiation image representing the bone portion and the reference substance by detecting radiation transmitted through the bone portion and the reference substance with a radiation detecting body;

obtaining a bone mineral density of the bone portion based on a radiation transmission characteristic of a section of the reference substance that indicates the same density as that of the analysis target bone portion in the radiation image;

driving the radiation tube with a plurality of tube voltages, including a normal tube voltage, and obtaining a radiation image of the reference substance under each tube voltage prior to obtaining the bone mineral density;

obtaining a density gradient with respect to at least two sections of the reference substance having different radiation transmission characteristics for each of the plurality of tube voltages from the radiation images of the reference substance; and correcting, if the radiation image captured for obtaining the bone mineral density is determined to have been captured under a tube voltage other than the normal tube voltage from a density gradient in the image, an image signal representing the image and/or a bone mineral density analysis result so as to correspond to that which should have been obtained if the image had been captured under the normal tube voltage based on the relationship between the density gradient in the image and the density gradient in the radiation image captured under the normal tube voltage.

3. The bone mineral density analysis method of claim 1, wherein an aluminum member whose thickness varies continuously or in a stepwise manner is used as the reference substance.

4. The bone mineral density analysis method of claim 3, wherein a bone mineral density is represented by a thickness of the aluminum member.

5. The bone mineral density analysis method of claim 1, wherein the radiation tube is set to a tube voltage of 50 kV as the normal state of the image capturing condition.

6. The bone mineral density analysis method of claim 1, wherein:

a plurality of radiation detecting bodies having different radiation absorption characteristics is usable as the radiation detecting body; and if one of the plurality of radiation detecting bodies other than a specific radiation detecting body is used, an image signal representing the radiation image used for obtaining the bone mineral density and/or a bone mineral density analysis result is corrected so as to correspond to that which should be obtained if the specific radiation detecting body were used.

7. The bone mineral density analysis method of claim 6, wherein a storage phosphor sheet is used as the specific radiation detecting body.

8. The bone mineral density analysis method of claim 2, wherein an aluminum member whose thickness varies continuously or in a stepwise manner is used as the reference substance.

9. The bone mineral density analysis method of claim 8, wherein a bone mineral density is represented by a thickness of the aluminum member.

10. The bone mineral density analysis method of claim 2, wherein the normal tube voltage is 50 kV.

11. The bone mineral density analysis method of claim 2, wherein:

a plurality of radiation detecting bodies having different radiation absorption characteristics is usable as the radiation detecting body; and if one of the plurality of radiation detecting bodies other than a specific radiation detecting body is used, an image signal representing the radiation image used for obtaining the bone mineral density and/or a bone mineral density analysis result is corrected so as to correspond to that which should be obtained if the specific radiation detecting body were used.

12. The bone mineral density analysis method of claim 11, wherein a storage phosphor sheet is used as the specific radiation detecting body.

13. A bone mineral density analysis system, comprising:

a radiation image capturing unit for projecting radiation generated from a radiation tube simultaneously onto an analysis target bone portion and a reference substance having a plurality of sections with different radiation transmission characteristics and obtaining a radiation image representing the bone portion and the reference substance by detecting radiation transmitted through the bone portion and the reference substance with a radiation detecting body;

a signal processing unit for obtaining a bone mineral density of the bone portion based on a radiation transmission characteristic of a section of the reference substance that indicates the same density as that of the analysis target bone portion in the radiation image;

a storage unit storing a density gradient with respect to at least two sections of the reference substance having different radiation transmission characteristics obtained, when an image capturing condition is sequentially changed to a plurality of different states, including a normal state, and a radiation image of the reference substance is obtained under each state prior to obtaining the bone mineral density, for each of the plurality of different states of the image capturing condition from the radiation images of the reference substance; and a correction unit for correcting, if the radiation image captured for obtaining the bone mineral density is determined to have been captured under a state other than the normal state from a density gradient in the image, an image signal representing the image and/or a bone mineral density analysis result so as to correspond to that which should have been obtained if the image had been captured under the normal state based on the relationship between the density gradient in the image and the density gradient in the radiation image captured under the normal state.

14. A bone mineral density analysis system, comprising:
a radiation image capturing unit for projecting radiation generated from a radiation tube simultaneously onto an analysis target bone portion and a reference substance having a plurality of sections with different radiation transmission characteristics and obtaining a radiation image representing the bone portion and the reference substance by detecting radiation transmitted through the bone portion and the reference substance with a radiation detecting body;
a signal processing unit for obtaining a bone mineral density of the bone portion based on a radiation transmission characteristic of a section of the reference substance that indicates the same density as that of the analysis target bone portion in the radiation image;
a storage unit storing a density gradient with respect to at least two sections of the reference substance having different radiation transmission characteristics obtained, when the radiation tube is driven with a plurality of tube voltages, including a normal tube voltage, and a radiation image of the reference substance is obtained under each tube voltage prior to obtaining the bone mineral density, for each of the plurality of tube voltages from the radiation images of the reference substance; and
a correction unit for correcting, if the radiation image captured for obtaining the bone mineral density is determined to have been captured under a tube voltage other than the normal tube voltage from a density gradient in the image, an image signal representing the image and/or a bone mineral density analysis result so as to correspond to that which should have been obtained if the image had been captured under the normal tube voltage based on the relationship between the density gradient in the image and the density gradient in the radiation image captured under the normal tube voltage.

15. A non-transitory computer readable recording medium on which is recorded a program for causing a computer to perform a bone mineral density analysis method, the medium recording the steps of:
projecting radiation generated from a radiation tube simultaneously onto an analysis target bone portion and a reference substance having a plurality of sections with different radiation transmission characteristics;
obtaining a radiation image representing the bone portion and the reference substance by detecting radiation transmitted through the bone portion and the reference substance with a radiation detecting body;
obtaining a bone mineral density of the bone portion based on a radiation transmission characteristic of a section of the reference substance that indicates the same density as that of the analysis target bone portion in the radiation image;
sequentially changing an image capturing condition to a plurality of different states, including a normal state, and obtaining a radiation image of the reference substance under each state prior to obtaining the bone mineral density;
obtaining a density gradient with respect to at least two sections of the reference substance having different radiation transmission characteristics for each of the plurality of different states of the image capturing condition from the radiation images of the reference substance; and
correcting, if the radiation image captured for obtaining the bone mineral density is determined to have been captured under a state other than the normal state from a density gradient in the image, an image signal representing the image and/or a bone mineral density analysis result so as to correspond to that which should have been obtained if the image had been captured under the normal state based on the relationship between the density gradient in the image and the density gradient in the radiation image captured under the normal state.

16. A non-transitory computer readable recording medium on which is recorded a program for causing a computer to perform a bone mineral density analysis method, the medium recording the steps of:
projecting radiation generated from a radiation tube simultaneously onto an analysis target bone portion and a reference substance having a plurality of sections with different radiation transmission characteristics;
obtaining a radiation image representing the bone portion and the reference substance by detecting radiation transmitted through the bone portion and the reference substance with a radiation detecting body;
obtaining a bone mineral density of the bone portion based on a radiation transmission characteristic of a section of the reference substance that indicates the same density as that of the analysis target bone portion in the radiation image;
driving the radiation tube with a plurality of tube voltages, including a normal tube voltage, and obtaining a radiation image of the reference substance under each tube voltage prior to obtaining the bone mineral density;
obtaining a density gradient with respect to at least two sections of the reference substance having different radiation transmission characteristics for each of the plurality of tube voltages from the radiation images of the reference substance; and
correcting, if the radiation image captured for obtaining the bone mineral density is determined to have been captured under a tube voltage other than the normal tube voltage from a density gradient in the image, an image signal representing the image and/or a bone mineral density analysis result so as to correspond to that which should have been obtained if the image had been captured under the normal tube voltage based on the relationship between the density gradient in the image and the density gradient in the radiation image captured under the normal tube voltage.

* * * * *